US007601487B2

(12) United States Patent
Soll et al.

(10) Patent No.: US 7,601,487 B2
(45) Date of Patent: Oct. 13, 2009

(54) COMPOSITION USING HMW DEXTRAN AND METHOD FOR IN VITRO PRESERVATION OF CORNEAL TISSUES (75) Inventors: David B. Soll, Ambler, PA (US); Inez A. Ruiz-White, Mount Laurel, NJ (US); Teresita M. Smith, Lake Forrest, CA (US)

(73) Assignee: Cleo Cosmetic and Pharmaceutical Co., LLC, Ambler, PA (US)

( * ) Notice: Subject to any disclaimer, the term of this patent is extended or adjusted under 35 U.S.C. 154(b) by 289 days.

(21) Appl. No.: 11/278,835

(22) Filed: Apr. 6, 2006

(65) Prior Publication Data

US 2006/0228693 A1  Oct. 12, 2006

Related U.S. Application Data (60) Provisional application No. 60/670,310, filed on Apr. 12, 2005.

(51) Int. Cl.
*A01N 1/00* (2006.01)
(52) U.S. Cl. ....................................................... 435/1.1
(58) Field of Classification Search ........................ None
See application file for complete search history.

(56) References Cited

U.S. PATENT DOCUMENTS

| | | | |
|---|---|---|---|
| 4,238,482 A | 12/1980 | Peyman | |
| 4,271,144 A | 6/1981 | Holly | |
| 4,695,536 A | 9/1987 | Lindstrom | |
| 4,713,375 A | 12/1987 | Lindstrom | |
| 4,844,242 A | 7/1989 | Chen | |
| 4,873,186 A | 10/1989 | Chen | |
| 4,886,786 A | 12/1989 | Lindstrom et al. | |
| 4,981,841 A | 1/1991 | Gibson | |
| 5,013,714 A | 5/1991 | Lindstrom | |
| 5,066,578 A | 11/1991 | Wikman-Coffelt | |
| 5,073,492 A | 12/1991 | Chen | |
| 5,104,787 A | 4/1992 | Lindstrom | |
| 5,166,048 A | 11/1992 | Soll | |
| 5,204,325 A | 4/1993 | Lindstrom | |
| 5,298,487 A | 3/1994 | Chen | |
| 5,306,711 A | 4/1994 | Andrews | |
| 5,326,699 A | 7/1994 | Torishima | |
| 5,366,964 A | 11/1994 | Lindstrom | |
| 5,405,742 A | 4/1995 | Taylor | |
| 5,407,669 A | 4/1995 | Lindstrom | |
| 5,589,451 A | 12/1996 | Wilson | |
| 5,599,659 A | 2/1997 | Brasile | |
| 5,643,712 A | 7/1997 | Brasile | |
| 5,654,266 A | 8/1997 | Chen | |
| 5,723,281 A | 3/1998 | Segall | |
| 5,827,641 A | 10/1998 | Parenteau | |
| 6,153,582 A | 11/2000 | Skelnik | |
| 6,162,642 A | 12/2000 | Redbrake-Adams | |
| 6,541,256 B1 | 4/2003 | Chen | |
| 6,645,715 B1 | 11/2003 | Griffith | |
| 6,706,499 B2 | 3/2004 | Mangnsson | |
| 6,838,448 B2 | 1/2005 | Ponzin | |
| 6,949,335 B2 | 9/2005 | Fahy et al. | |
| 2001/0055809 A1 | 12/2001 | Mangat | |
| 2002/0081289 A1 | 6/2002 | Neuhann | |
| 2002/0103222 A1 | 8/2002 | Mangat | |
| 2002/0132220 A1 | 9/2002 | Berens | |
| 2003/0149002 A1 | 8/2003 | Goddard | |
| 2004/0142466 A1 | 7/2004 | Mangat | |
| 2004/0185561 A1 | 9/2004 | Cook | |

FOREIGN PATENT DOCUMENTS

| | | |
|---|---|---|
| EP | 0 562 188 B1 | 9/1992 |
| EP | 0 516 901 A1 | 12/1992 |
| EP | 0 517 972 B1 | 12/1992 |
| JP | 02-005859 | 1/1990 |
| JP | 02-113885 | 4/1990 |
| JP | 05-025001 | 2/1993 |
| WO | WO 97/37537 | 10/1997 |
| WO | WO 00/47040 A1 | 8/2000 |

OTHER PUBLICATIONS

Medum 199 Modified (M199):, JRH Biosciences, Product Information, Catalog No. 51312, 1 page (2005).*
Wang et al., "Use of carnosine as a natural anti-senescence drug for human beings.", *Biochemistry*, vol. 65(7), pp. 869-871 (2000).
Hipkiss et al., "Carnosine reacts with protein carbonyl groups: Another possible role for the anti-ageing peptide?", *Biogerontology*, vol. 1(3), pp. 217-223 (2000).
Hipkiss et al., "A possible new role for the anti-ageing peptide carnosine", *CMLS Cell. Mol. Life Sci.*, vol. 57, pp. 747-753 (2000).
Camposampiero et al., "Cornea preservation in culture with bovine serum or chicken ovalbumin", *Cornea*, vol. 22(3), pp. 254-258 (2003).
Redbrake, et al., "Correlation between glucose and lactate concentrations in the human cornea and in organ culture medium", *Klin Monatsb. Augerheilkd*, vol. 213, pp. 93-96, 1 page (1998).
"Organ preservation protocols", Catholic University of Louvain, St.—Luc University Hospital Head and Neck Oncology Progamme, *Organ Preserv.* 11 pages (2001).

(Continued)

*Primary Examiner*—Sandra E. Saucier
(74) *Attorney, Agent, or Firm*—Panitch Schwarze Belisario & Nadel LLP (57) ABSTRACT A corneal storage solution which maintains cell density and cell viability of corneas stored in vitro for a period of greater than four days up to about two weeks is provided. The solution contains a buffered, balanced, nutrient and electrolyte aqueous solution, at least one colloidal osmotic agent, a phenolic antioxidant compound, a non-lactate-generating substrate, a thiol-containing compound, insulin, and at least one antibiotic. A method for in vitro storage and preservation of the viability of human corneal endothelial cells for subsequent use includes the steps of removing a cornea from an eye globe and placing the cornea in the above corneal storage solution.

30 Claims, 3 Drawing Sheets

OTHER PUBLICATIONS

Chen et al., "The Efficacy of Non-Lactate-Generating Metabolites as Substrates for Maintaining Donor Tissues", *Transplantation*, vol. 57, No. 12, pp. 1778-1785, (1994).

Hiebert, et al., "Protective Action of Polyelectrolytes on Endothelium", *Seminars in Thrombosis and Hemostasis*, vol. 17, Supplement 1, pp. 42-46 (1991).

Lindstrom, "Advances in Corneal Preservation", Tr. Am. Ophth. Soc., Vol. LXXXVIII, pp. 555-648, (1990).

Cornea Donor Study Group, "An Evaluation of Image Quality and Accuracy of Eye Bank Measurement of Donor Cornea Endothelial Cell Density in the Specular Microscopy Ancillary Study", American Academy of Ophthalmology, *Opthamology*, vol. 112, No. 31, pp. 431-440 (2005).

Middleton, Jr. et al., "The Effects of Plant Flavonoids on Mammalian Cells: Implications for Inflammation, Heart Disease, and Cancer", *Pharmacol Reviews*, vol. 52, pp. 673-751 (2000).

Zeng et al., "Morin hydrate: a better protector than purpurogallin of corneal endothelial cell damage induced by xanthine oxidase and SIN-1", *Curr. Eye Res.*, vol. 17, pp. 149-152 (1998).

Fang et al., "Morin sulfates/glucuronides exert anti-inflammatory activity on activated macrophages and decreased the incidence of septic shock", *Life Sciences*, vol. 74, pp. 743-756 (2003).

Hull et al., "Dextran uptake into, and loss from, corneas stored in intermediate-term preservative", *Investigative Ophthalmology*, vol. 15, No. 8, pp. 663-666 (1976).

Ediriwickrema et al., "Natural killer cell-dependent immunoglobulin G2a anti-bovine serum albumin (BSA) response elicited by high molecular weight dextran-BSA conjugates associated with dextran-mediated macrophage-natural killer cell interaction", *Immunology*, vol. 101, pp. 474-483 (2000).

Halberstadt et al., "Corneal Cryopreservation with Dextran", *Cryobiology*, vol. 43, pp. 71-80 (2001).

Jagodzinski et al., "The effect of high molecular weight dextran sulfate on the production of interleukin-8 in monocyte cell culture", *Biomed Pharmacother*, vol. 56, pp. 254-257 (2002).

Chen et al., "Efficacy of Media Enriched with Nonlactate-Generating Substrate for Organ Preservation: In Vitro and Clinical Studies Using the Cornea Model[1,2]", *Transplantation*, vol. 67(6), pp. 800-808 (1999).

Nakamura et al, "Protective Effect of D-β-Hydroxybutyrate on Corneal Epithelia in Dry Eye Conditions through Suppression of Apoptosis", *Investigative Ophthamology & Visual Science*, vol. 44, No. 11, pp. 4682-4688 (2003).

Rocha et al., "Identification of Insulin in the Tear Film and Insulin Receptor and IGF-I Receptor on the Human Ocular Surface", *Investigative Ophthamology & Visual Science*, vol. 43, No. 4, pp. 963-967 (2002).

Imanishi et al., "Growth Factors: Importance in Wound Healing and Maintenance of Transparency of the Cornea", *Progress in Retinal and Eye Research*, vol. 19, No. 1, pp. 113-129 (2000).

Chen et al., "Efficacy of Organ Preservation Media Enriched with Nonlactate-Generating Substrate for Maintaining Tissue Viability: A Transplantation Study", *Transplantation*, vol. 63(5), pp. 656-663 (1997).

Chin Fook et al., "The Prevention of Autolysis of Stored Cornea Using Steroid as a Lysosome Membrane Stabilizer", *Canad. J. Ophthal.*, vol. 10, pp. 482-486 (1975).

Travkin et al., "Effect of Antioxidants with Different Antiradical Activity on Cornea Preservation", Biofizika, vol. 21(6), pp. 1064-1066 (1976).

Basu et al., "The Prevention of Autolysis in Stored Corneas by Lysosome Stabilization. A Histochemical Study", *Canad. J. Ophthal.*, vol. 12, pp. 48-53 (1977).

Spencer et al., "Factors in the Survival of Stored Corneas", *Canad. J. Ophthal.*, vol. 12, pp. 123-127 (1977).

Basu et al., "Can Steroid Reduce Endothelial Damage in Stored Corneas? Effect on Cell Viability and Ultrastructure", *Canad. J. Ophthal.*, vol. 13, pp. 31-38 (1978).

Liao et al., "Biochemical Analysis of the Cornea Stored in Steroid Medium", *Canad. J. Ophthal.*, vol. 14, pp. 274-280 (1979).

Hull et al., "Corneal Endothelial Cell Function after Storage in MK Medium and Hydrocortisone", *Canad. J. Ophthal.*, vol. 14, pp. 114-116 (1979).

Basu et al., "Damage to Corneal Endothelial Cells by Lysosomal Enzymes in Stored Human Eyes", *Canad. J. Ophthal.*, vol. 15, pp. 137-140 (1980).

Basu et al., "Preventing Corneal Autolysis after a Donor's Death", *Can. J. Ophthalmol.*, vol. 17(2), pp. 70-73 (1982).

Morgan et al., "Lysosomal Enzyme Levels in Corneal Storage Media:K-Sol versus McCareyKaufman", *Ophthalmology*, vol. 95(11), pp. 1498-1503, (1988).

Hasany et al., "Changes of MK Medium During Storage of Human Cornea", *British Journal of Ophthalmology*, vol. 71, pp. 477-483 (1987).

Yap et al., "Corneal Temperature Reversal After Storage in Chen Medium Compared With Optisol GS", *Cornea*, vol. 20(5), pp. 501-504 (2001).

Nelson et al., "In Vitro Comparison of Chen Medium and Optisol-GS Medium for Human Corneal Storage", *Cornea*, vol. 19(6), pp. 782-787 (2000).

Bourne et al., "Comparison of Chen Medium and Optisol-GS for Human Corneal Preservation at 4° C.", *Cornea*, vol. 20(7), pp. 683-686 (2001).

Doughman, "Prolonged Donor Cornea Preservation in Organ Culture", *Transactions of the American Ophthalmological Society*, vol. 78, pp. 568-628 (1980).

Woost et al., "Growth Factors and Corneal Endothelial Cells: I. Stimulation of Bovine Corneal Endothelial Cell DNA Synthesis by Defined Growth Factors", *Cornea*, vol. 11(1), pp. 1-10 (1992).

Morgan et al., "The Nutrition of Animal Tissues Cultivated In Vitro. I. A Survey of Natural Materials as Supplements to Synthetic Medium 199", *Journal of the National Cancer Institute*, vol. 16(2), pp. 557-558 (1955).

Evans et al., "Studies of Nutrient Media for Tissue Cells in Vitro. I. A Protein-free Chemically Defined Medium for Cultivation of Strain L Cells", *Journal of the National Cancer Institute*, pp. 77-82 (1955).

Morgan et al., "Nutrition of Animal Cells in Tissue Culture. I. Initial Studies on a Synthetic Medium", *Proceedings of the Society for Experimental Biology and Medicine*, vol. 73(1), pp. 1-8 (1950).

Bourne et al., "Endothelial Cell Survival on Transplanted Human Corneas Preserved by Organ Culture with 1.35% Chondroitin Sulfate", *American Journal of Ophthalmology*, vol. 100, pp. 789-793 (1985).

SIGMA—Product Information, "Medium 199", 7 pages (2006).

Woost et al., "Enhancement of corneal endothelial cell mitosis in corneal storage medial using EGF and other defined agents," *Invest. Opthal. Vis. Sci.*, vol. 29, p. 112 (1988).

Reddy et al., "Endothelial cell damage in human and rabbit corneas stored in K-Sol without antioxidants," *Br. J. Ophthal.*, vol. 73/10, pp. 308-808 (1989).

SIGMA—Product Information, "Minimum Essential Medium Eagle (MEM)", 6 pages (2006).

Crow et al., "Effects of Insulin and EGF on DNA Synthesis in Bovine Endothelial Cultures: Flow Cytometric Analysis", *Investigative Ophthalmology & Visual Science*, vol. 35(1), pp. 128-133 (1994).

Bigar et al., "Improved corneal storage: Penetrating keratoplasties in rabbits", *Exp. Eye Res.*, vol. 20(3) pp. 219-222 (1975).

Van Horn et al., "Endothelial survival in corneal tissue stored in M-K medium", *Am J Ophthalmol*, vol. 80(4), pp. 642-647 (1975).

Breslin et al., McCarey-Kaufman technique of corneal storage before penetrating keratoplasties in rabbits, *Arch Ophthalmol*, vol. 94, pp. 1976-1979 (1976).

Binder et al., "M-K medium and postmortem cytologic damage", *Invest Ophthalmol Vis Sci.*, vol. 17(2), pp. 159-170 (1978).

Kaufman et al., "Chondroitin sulfate in a new cornea preservation medium", *Am. J Ophthalmol*, vol. 98, pp. 112-114 (1984).

Bourne, "Morphologic and functional evaluation of the endothelium of transplanted human corneas", *Tr. Am Ophth. Soc.*, Vol. LXXXI, pp. 403-450 (1983).

Nelson et al., "McCarey-Kaufman (MK) organ culture and MK medium-shifted corneas", *Arch Ophthalmol*, vol. 102, pp. 308-311 (1984).

Kaufman et al., "K-Sol corneal preservation", *Am. J Ophthalmol*, vol. 100(2), pp. 299-304 (1985).

Lindstrom et al., "Minnesota System Corneal Preservation", *Dev. Ophthalmol*, vol. 11, pp. 37-43 (1985).

Busin et al., "Comparison of K-Sol and M-K medium for cornea storage: results of penetrating keratoplasty in rabbits", *Br J Ophthalmol*, vol. 70(11), pp. 860-863 (1986).

Lass et al., "Effects of moist-chamber and McCarey-Kaufman medium storage on the metabolic status of the cornea: A 31 P-magnetic resonance analysis", *Ophthalmic Res.*, vol. 20, pp. 368-375 (1988).

Wong et al., "Corneal graft survival in the cat with prolonged preservation in McCarey-Kaufman and K-Sol media", *Arch Ophthalmol*, vol. 106, pp. 981-985 (1988).

Tamaki et al., "K-Sol corneal preservation at room temperature", *Br. J Ophthalmol*, vol. 72(5), pp. 370-376 (1988).

Kaufman et al., "Optisol Corneal Storage Medium", *Arch Ophthalnnol*, vol. 109(6), pp. 864-868 (1991).

Lindstrom et al., "Optisol Corneal Storage Medium", *Am J Ophthalmol*, Vol. 114(3), pp. 345-356 (1992).

"Facts About the Cornea and Corneal Disease"; [online] retrieved from www.nei.nih.gov/health/cornealdisease/; [retrieved on Jun. 17, 2003] 17 pages.

"New organ preservation solution easier to use" ; [online] retrieved from www.eurekalert.org/pub_releases; [retrieved on Jun. 17, 2003] 2 pages.

"New Organ Preservation Solution Easier to Use and More Cost Effective than Standard UW Solution, Says University of Pittsburgh Study" ; [online] retrieved from www.newsbureau.upmc.com/CurrentReleases; [retrieved on Jun. 17, 2003] 2 pages.

"Organ Preservation for Transplantation"; [online] retrieved from www.ualberta.ca/smri/Organ%20Preservation; [retrieved on Jun. 17, 2003] 2 pages.

Southard, "Organ Preservation for Transplantation" [online]; retrieved from www.surgery.wisc.edu/transplant/ research/grant; [retrieved on Jun. 17, 2003] 2 pages.

"Biology Researchers Testing Organ Preservation Device" [online]; retrieved from www.uakron.edu/news/articles; [retrieved on Jun. 17, 2003] 1 page.

"Antifreeze Protein Holds Promise for Organ Preservation" [online]; retrieved from www.sciencedaily.com/releases/1998; [retrieved on Jun. 17, 2003] 2 pages.

Baicu et al., "Acid-Base Buffering in Organ Preservation Solutions as a Function of Temperature: New Parameters for Comparing Buffer Capacity and Efficiency"; Abstract from XIX International Congress of The Transplantation Society; 1 page (2002).

"Technical Resources—Invitrogen Media Formulations—Medium 199 (1X) liquid" [online]; retrieved from www.invitrogen.com/content; [retrieved on Mar. 29, 2005] 4 pages.

Kaufman et al., "Structure and Function of the Cornea"; The Cornea Second Edition on CD-ROM—Companion Handbook to the Cornea [CD-ROM]; retrieved from CD-ROM [retrieved on Jun. 17, 2003]; 5 pages (2000).

* cited by examiner

COMPOSITION USING HMW DEXTRAN AND METHOD FOR IN VITRO PRESERVATION OF CORNEAL TISSUES

CROSS-REFERENCE TO RELATED APPLICATIONS

This application claims the benefit of U.S. Provisional Patent Application No. 60/670,310, filed Apr. 12, 2005; the disclosure of which is herein incorporated by reference.

BACKGROUND OF THE INVENTION

The cornea is the eye's outermost layer. It is a clear, dome-shaped surface that covers the front of the eye. The corneal structure is a highly organized group of cells and proteins. To see well, all layers of the cornea must be free of any cloudy or opaque areas.

Corneal tissue comprises five basic layers: the epithelial layer, Bowman's layer, the stroma, Decemet's membrane, and the endothelial layer. The cells of the endothelial layer play the most significant role in keeping the cornea clear. Under normal conditions, fluid travels slowly from the inside of the eye into the middle of the corneal layer (stroma). The endothelium's primary task is to pump this excess fluid out of the stroma. Without this pumping action, the stroma would swell with water, become hazy, and ultimately become opaque. Often due to pathology or an injury, endothelial cells may be destroyed. For all practical purposes, corneal endothelial cells do not reproduce. Thus, when endothelial cells are lost, either by trauma or disease, the lost cells are not replaced, and adjacent endothelial cells migrate and expand into the defect.

Corneal edema (swelling) occurs when the endothelial cell density is below a certain level, usually below about 400 cells/mm$^2$. At birth, endothelial density varies between about 3,500 and 4,000 cells/mm$^2$ (Kaufman et al. *The Cornea*; Second Edition on CD-Rom; Butterworth-Heinemann (1999)). As individuals age, there is a gradual attrition of corneal endothelial cells, so that when a normal individual reaches the age of 70 or older, the endothelial cell count may be only 2,500 cells/mm$^2$. Clear vision depends on corneal clarity, which in turn depends on corneal deturgesence. Advanced corneal swelling is associated with severe vision loss and blindness. Corneal opacities due to disease or scarring are also associated with visual loss and, if severe, blindness.

Corneal transplantation is the only available therapy to remedy irreversible corneal edema or scarring. Corneal transplant therapy involves replacing the diseased, scarred or traumatized cornea with a healthy, clear cornea obtained from an organ donor. Corneal transplants are very common in the United States—it is reported that upwards of 50,000 are performed per year with a larger number being performed worldwide. Such procedures have a success rate of about 85%, making them the most successful type of surgical transplant procedures being performed.

As in other cases of organ transplantation, it is necessary to perform various tests on the donor's blood to rule out various infectious diseases that may be transmitted to the recipient, resulting in a delay in the surgical procedure being performed. Not infrequently, donor tissue must be transported, causing further delay. Therefore, it is necessary to undertake in vitro storage or maintenance of the harvested tissue and cells until transplantation occurs. With a donor cornea, the corneal tissue must be preserved in a way that the viability and density of the corneal cells, particularly those of the endothelial layer, are preserved, and that the cornea does not swell and maintains its clarity.

Various solutions and media have been developed to preserve tissues for storage and/or transportation for later use. However, even with specially prepared available storage media, the practical storage life is limited. For example, the widely used McCarey-Kaufman medium is considered to be useful in the preservation of corneal tissues for up to four days. The most commonly used medium in U.S. eyebanks for corneal preservation is the commercially available Optisol™ solution (Bausch & Lomb), designed for intermediate storage at 4° C. Optisol™ solution is a serum-free medium containing a base medium, a buffer, chondroiton sulfate, dextran (molecular weight 40K), vitamins, and ATP precursors. Although studies, (e.g., Kaufman et al. *Arch Ophthalmol;* 109:864-868 (1991); Lindstrom et al. *Am Journal of Ophthalmol;* 114:345-346 (1992)) have reported that Optisol™ is effective at preserving endothelial structure for up to two weeks, there is a significant loss of endothelial viability after this time and the majority of surgeons prefer not to use a cornea which has been stored for more than about five days in this medium. There is therefore a need in the art to develop an improved corneal storage medium that facilitates the preservation of corneal tissue over a longer period of time.

BRIEF SUMMARY OF THE INVENTION

A corneal storage solution is provided which comprises:
(a) a buffered, balanced, nutrient and electrolyte aqueous solution;
(b) at least one colloidal osmotic agent;
(c) a phenolic antioxidant compound;
(d) a non-lactate generating substrate;
(e) a thiol-containing compound;
(f) insulin; and
(g) at least one antibiotic;

in amounts effective to maintain cell density and cell viability of corneas stored in vitro for a period of greater than four days up to about two weeks; wherein components (b) to (g) are only required to the extent that they are not included in (a).

The invention also provides a method for the in vitro storage and preservation of the viability of human corneal endothelial cells for subsequent use, comprising the steps of:
(a) removing a cornea from an eye globe; and
(b) placing the cornea in the corneal storage solution as previously described.

Finally, a kit is provided which comprises:
(a) a vial having a flat, optically clear bottom; and
(b) the corneal storage solution as previously described.

DETAILED DESCRIPTION OF THE INVENTION

The invention provides an improved corneal storage solution useful for the in vitro storage and preservation of corneal tissues. The solution preserves and maintains the cell viability, structural integrity, and cell density of corneal tissues, rendering them useful for subsequent transplantation, cell culture, and/or grafting therapies. Usage of this storage solution allows corneas to be stored for more than about four days up to at least about two weeks.

Specifically, the corneal storage solution comprises effective amounts of:

(a) a buffered, balanced nutrient and electrolyte aqueous solution;
(b) at least one colloidal osmotic agent;
(c) a phenolic antioxidant compound;
(d) a non-lactate generating substrate;
(e) a thiol containing compound;
(f) insulin; and
(g) at least one antibiotic.

Each of components (b) to (g) is only required to the extent that it is not included in the nutrient and electrolyte solution (a). That is, if a nutrient and electrolyte solution which contains one or more of these components is utilized, it may not be necessary to add an additional amount of the component (b) to (g), unless the concentration in (a) is not at the desired level.

Each of the components of the corneal storage solution will now be described in detail.

Nutrient and Electrolyte Solution

The buffered, balanced nutrient and electrolyte aqueous solution for use in the invention is preferably M-199 (medium 199), a product which is commercially available from a variety of sources such as Mediatech, Inc. However, other similar solutions which are known in the art or to be developed would also be appropriate for use in the invention, including without limitation Ham's F12 and MEM (minimal essential media). The formulation of M-199 is well-known, and contains various amino acids, vitamins, inorganic salts, ATP precursors, and other components, including a Hepes (hydroxyethylpiperizine ethane sulfonic acid) buffer. A phenol red or similar indicator for visual determination of undesirable changes in pH, which would make the storage solution unacceptable for use, is also preferably included, but may be separately added to the corneal storage solution if not present in the nutrient solution. The amount of indicator which is utilized may be determined by routine experimentation.

The presence of the Hepes buffer maintains the pH of the storage solution at about 7.2 to about 7.4. Thus, if a nutrient and electrolyte solution which does not contain a buffer is to be utilized or if the amount of buffer is insufficient, a separate buffer is preferably included in the storage solution, so that the pH can be adjusted to the preferred range of about 7.2 to about 7.4.

The M-199 nutrient solution contains about twenty different amino acids. However, one or more of these amino acids could be eliminated from the storage solution according to the invention without affecting its efficacy, and the nutrient solution for use in the invention preferably contains at least about fifteen amino acids.

Colloidal Osmotic Agent

A second important component of the solution is a colloidal osmotic agent, which is included to maintain the morphology of the cell and to prevent corneal swelling. For example, appropriate colloidal osmotic agents for use in the storage solution include high molecular weight dextran, chondroitin sulfate, and hydroxyethyl starch. The colloidal osmotic agent is preferably present in the solution in an amount of about 1 to about 10 weight %. In preferred embodiments, the solution contains high molecular weight dextran, either alone or in addition to chondroiton sulfate.

Dextran is a glucose polymer with a chain-like structure which exists at various molecular weights. It is known that dextran acts as a colloidal osmotic agent which prevents excessive corneal swelling (Hull et al. *Investigative Opthalmology;* 663-666 (1976)). The commercially available Optisol™ solution contains 1% dextran having a molecular weight of about 40,000 Daltons. However, it has been reported that high molecular weight dextran fractions (having molecular weights greater than about 500 kDa) can activate immune cells and protect endothelial cells from free-radical damage (Hiebert et al. *Seminar in Thrombosis & Hemostasis;* 17:42-46 (1991); Ediriwickremab et al. *Immunology;* 101: 474-483 (2000); Halberstadt et al. *Cryobiology.* 43:71-80 (2001); Jagodzinski et al. *Biomed Pharmacother;* 56:254-257 (2002)).

For these purposes, as well as to maintain cell morphology and to prevent corneal swelling, the corneal storage solution according to the invention preferably contains high molecular weight dextran, more preferably dextran having a molecular weight of about 2,000,000 Daltons. However, for use in the invention, the term "high molecular weight dextran" encompasses dextran having a molecular weight of at least about 500,000 Daltons. It is presently preferred to utilize water soluble dextran fractions so that the resulting storage solution will be homogeneous. The storage solution preferably contains about 0.25% to about 2.5% by weight high molecular weight dextran (about 2.5 to about 25 g/L), more preferably about 1 weight % (about 10 g/L). When dextran is utilized in the solution without chondroitin sulfate, the dextran is preferably present in an amount of about 10 weight %.

Another preferred colloidal osmotic agent, which is preferably included in addition to high molecular weight dextran, is chondroiton sulfate. Chondroitin sulfate prevents corneal swelling and maintains deturgescence (balance of hydration) in the eye. The chondroiton sulfate is preferably present in an amount of about 1% to about 7.5% by weight (about 10 to about 75 g/L), more preferably about 3% to about 5% by weight (about 30 to about 50 g/L).

Chondroitin sulfate is a sulfate acid mucopolysaccharide, which is a normal component of human corneas, and is ubiquitous in animal tissue. It is a viscous substance that has a molecular weight of about 50,000 to 100,000 Daltons depending on the source, although lower molecular weight species on the order of about 20,000 to 50,000 Daltons are also sometimes present. Chondroitin sulfate is effective in the present invention at all molecular weights.

Chondroitin sulfate has five isomers (chondroitin sulfates A, B, C, D, and E) that are characterized by a sulfate group taking one of five positions in the repeating N-acetylchondrosin disaccharide unit. Each repeating disaccharide unit has one sulfate group. (See *The Merck Index*, monograph 2235, pages 383-384 (13$^{th}$ Ed. 2001)). The most common isomers of chondroitin sulfate are "A", "B", and "C".

Chondroitin sulfates A and C both contain D-glucuronic acid, 2 amino-2 deoxy-D-galactose, acetyl and sulfate residues in equimolar quantities. There is a close similarity in structure between chondroitin sulfates A and C, demonstrated by the fact that both afford the same disaccharide, chondrosine, in high yields on acidic hydrolysis. These two mucopolysaccharides are distinguished by their optical rotation and by the solubility of their calcium salts in aqueous ethanol. Chondroitin sulfates A and C structurally differ only in the position of the sulfate ester grouping in the hexosamine residue; the sulfate ester occurs at carbon-4 in the chondroitin sulfate A and at carbon-6 in the chondroitin sulfate C. The nature of the hexuronic acid (L-iduronic acid) of chondroitin sulfate B serves to distinguish it from other isomeric chondroitin sulfates.

Any isomeric form of chondroitin sulfate (A, B, C, D, or E) may be utilized in the present solution. Chondroitin sulfate A may be derived from whale cartilage; chondroitin sulfate B may be derived from porcine skin; and chondroitin sulfate C may be derived from shark cartilage. A fairly plentiful source for chondroitin sulfate is the nasal septa of cows. Chondroitin sulfate also exists in the trachea, aorta, tendons and other parts of the animal body. Certain sections of domesticated animal cartilage contain up to 40% chondroitin sulfate by weight. All forms of chondroitin sulfate with varying sulphur contents essentially have the same mechanism of protective action and would therefore be effective in the present invention. However, the preferred isomer for use in the corneal storage solution is isomer "C", which exhibits particularly high purity and potency.

Phenolic Antioxidant Compound

A third component of the storage solution is a phenolic antioxidant compound, such as, but not limited to a flavanoid. Flavonoids are the most abundant polyphenolic compounds present in the human diet and have been demonstrated to be associated with a variety of biochemical and pharmacological properties, including antioxidant, antiviral, anticarcinogenic, and anti-inflammatory activities (Middleton et al. *Pharmacol Rev*; 52:673-751 (2000)). The phenol and hydroxyl groups of the flavanoids are both important for providing their antioxidant activity. Exemplary flavanoids which may be used in the storage solution according to the invention include resveratrol, fistein, piceatannol, quercetin, butein, rutin, gallic acid, green tea extract, and morin, which is presently preferred.

Morin is a flavonoid which is present in fruits, Brazil wood, and Chinese herbs and has specifically been shown to serve as a broad-spectrum antioxidant by scavenging not only xanthine oxidase/hypoxanthine-generated oxyradicals, but also by scavenging non-enzymatic and nitrogen-derived radicals (Zeng et al. *Curr Eye Res*; 1998; 17:149-152 (1998); Fang et al. *Life Sci*; 74:743-756 (2003)). Further, morin prolongs the survival of corneal endothelial cells (Fang et al. *Life Sci*; 74:743-756 (2003)). Morin is commercially available from Sigma and VWR.

It is also within the scope of the invention to include a phenolic antioxidant which is not a flavanoid, such as capsaicin. A non-flavanoid phenolic antioxidant may be included instead of or in addition to a flavanoid.

The corneal storage solution according to the invention preferably contains about 10 μM to about 2 mM phenolic antioxidant compound, more preferably about 100 μM to about 1 mM, most preferably about 300 μM.

Non-lactate Generating Substrate

The solution preferably contains a non-lactate generating substrate, that is, a substrate which does not generate lactate. This substrate functions as an energy source, and may be, without limitation, acetoacetate, β-hydroxybutyrate and derivatives thereof, β-hydroxyhaxonate and derivatives thereof, and L-lactide. It is presently preferred to utilize β-hydroxybutyrate. Any optical isomer of β-hydroxybutyrate (including the D isomer, the L isomer, or the D,L-racemate) may be used. β-hydroxybutyrate is a ketone body having the ability to be converted to acetyl-CoA (acetyl coenzyme A), which generates energy in the form of ATP. β-hydroxybutyrate reduces lactate formation and maintains ATP and metabolic activity in corneas (Chen et al. *Transplantation*; 57:1778-1785 (1994)). Further, β-hydroxybutyrate (a non-lactate generating substrate) (see Chen et al. *Transplantation*; 67:800-808 (1999); Chen et al. *Transplantation*; 63:656-663 (1997)) is present in known organ storage media and has been demonstrated to maintain corneal epithelial cell viability (Nakamura et al. *Investigative Ophthalmology & Visual Science*; 44:4682-4688 (2003)). The corneal storage solution according to the invention preferably contains about 5 mM to about 35 mM non-lactate generating substrate, more preferably about 10 mM.

Thiol-containing Compound

A further important component of the storage solution is a thiol-containing compound, such as mercapto acetic acid, N-acetyl-L-cysteine, β-mercaptoethanol, cysteine, dithiothreitol, cystein methyl ester, or the preferred thio-containing compound, glutathione (reduced). The thiol-containing compound acts as a chelator and a free radical scavenger. The thiol-containing compound is preferably present in the storage solution at a concentration of about 50 μM to about 2 mM, more preferably about 500 μM. While glutathione (reduced) may be present in the base nutrient and electrolyte solution, it may be desirable to add additional glutathione to increase the concentration to the preferred concentration range. However, as noted above, if the concentration of glutathione in the nutrient and electrolyte solution is in the preferred concentration range, it need not be specifically added to form the inventive solution. Any isomer of glutathione may be utilized in the storage solution, but the "L" isomer is presently preferred.

Insulin

A further important component of the corneal storage solution is insulin. Insulin is a hormone which is essential for tissue development, tissue growth, and glucose homeostasis. Insulin has been detected in tear film and in corneal epithelial, keratocyte, and endothelial cells, and is suggested to play a role in the metabolic and/or mitogenic processes (Rocha et al. *Investigative Ophthalmology & Visual Science* 963-967 (2002); Imanishi et al. *Progress in Retinal & Eye Research* 19:113-129 (2000)). It is preferred that the insulin be present in the solution at a concentration of about 0.001 mg/ml to about 0.012 mg/ml, more preferably about 0.006 mg/ml. It is preferred that the insulin utilized in the storage solution be human recombinant insulin which is less likely to be immunogenic.

Antibiotic

Finally, the corneal storage solution according to the invention preferably contains at least one antibiotic. A preferred solution contains about 200 μg/ml streptomycin and about 100 μg/ml gentamycin. Other antibiotics which are known or to be developed, such as penicillin and erythromycin, either alone or in combination, would also be appropriate for inclusion in the solution, and are preferably present in the solution at a concentration of about 10 μg/ml to about 1000 μg/ml. Broader spectrum antibiotics from the new generation of fluoroquinolones, such as moxifloacin and gatifloxacin, would also be suitable for use in the solutions. It is preferred that if a fluoroquinolone antibiobic is utilized, it is provided at a concentration of about 1 mg/ml to about 15 mg/ml. If the antibiotic is a high potency broad spectrum antibiotic, which will be effective at killing both positive and negative bacterial strains, it is preferable to include only one antibiotic in the solution. However, if a narrower spectrum antibiotic is selected, it may be desirable to include more than one antibiotic.

Additional Components

A variety of additional components may also be included in the storage solutions. For example, it may be desirable to include one or more additional antioxidants in the composition in addition to the phenolic antioxidant. For example, antioxidants which would be appropriate include, without limitation, selenium, hydralazine, lutein, alpha-tocopherol, Trolox (vitamin E), and ascorbic acid (vitamin C), which is presently preferred. If included, the antioxidant(s) are preferably present at a concentration of about 100 μM to about 1 mM. The preferred ascorbic acid is preferably present at a concentration of about 0.018 to about 0.176 g/L (about 100 μM to about 1 mM), more preferably about 0.045 g/L (about 250 μM).

It may also be desirable to include carnosine and/or a derivative thereof in the corneal storage solution. In addition to functioning as antioxidants, carnosine and carnosine derivatives have been reported to retard and rejuvenate senescence, as well as to preserve cellular integrity. The terms "carnosine" and "carnosine derivatives" as used herein include all isomeric forms, particularly beta-alanyl-L-histidine ("L-carnosine"), derivatives of L-carnosine and the pharmaceutically acceptable salts of L-carnosine (for example, the sodium, potassium, and/or hydrochloride salts). Also included within the meaning of these terms are acetyl carnosines, such as N-acetyl-carnosine, N-acyl-carnosine, homo-carnosine (gamma-aminobutyric acid-L-histidine), methyl-carnosine, ethylestercarnosinate, dimethylcarnosine, the reduced amide form of carnosine, and the ethyl esters of carnosines or carnosine derivatives in which the ester moiety contains about 1 to 5 carbon atoms and may be branched or unbranched.

Other additional components which may be included in the storage solutions include calciferol, i-inositol, inosine, sodium bicarbonate, sodium pyruvate, and L-alanyl-L-glutamine. Calciferol (vitamin D) is desirable to dissolve fats, and is involved in the overall health and storage of cells. Calciferol is preferably present in the solution at an amount of up to 0.0002 g/L, more preferably about 0.0001 g/L. i-Inositol (vitamin $B_8$) may be included in the solution to affect the signal transduction of phospholipids, metabolic regulation, and growth at a concentration of up to about 0.0001 g/L, more preferably about 0.00005 g/L. Calciferol and i-inositol are typically present in the nutrient and electrolyte solution, but it may be desirable to adjust the concentrations of these components to within the desired ranges.

To improve ATP production, it may be desirable to include inosine in the storage solution at a concentration of up to about 0.01 g/L, more preferably about 0.005 g/L. Sodium bicarbonate may be included in the composition in an amount of about 1.3 to about 2.5 g/L, more preferably about 1.7 g/L. Sodium bicarbonate interacts with hydrogen ions and carbon dioxide to buffer acidosis. It may be desirable to include sodium pyruvate, a critical component of the Krebs cycle, to support ATP production, preferably at a concentration of about 0.9 to about 1.1 mM, more preferably about 1 mM. Finally, another component which may be added to the solution is L-alanyl-L-glutamine, an essential amino acid which is critical to cellular growth, metabolism, and endurance, preferably at a concentration of about 3.6 to about 4.4 mM, more preferably about 4 mM.

The components of a preferred embodiment of the corneal storage solution according to the invention are shown in Table 1 with the possible concentration ranges and preferred approximate concentrations.

TABLE 1

Corneal Storage Solution

| Component | Possible Concentration | Preferred Approximate Concentration |
|---|---|---|
| M199 | balance | |
| L-glutamine | 3.6-4.4 mM | 4 mM |
| Hepes | to pH 7.2 to 7.4 | |
| Sodium bicarbonate | 1.3-2.5 g/L | 1.7 g/L |
| Sodium pyruvate | 0.9-1.1 mM | 1 mM |
| Streptomycin | 10-1000 μg/ml | 200 μg/ml |
| Gentamycin | 10-1000 μg/ml | 100 μg/ml |
| Phenol Red indicator | if needed | |
| Inosine | 0-0.01 g/L | 0.005 g/L |
| High Molecular Weight Dextran | 2.5-25 g/L | 10 g/L |
| Chondroitin Sulfate C | 10-75 g/L | 30 g/L |
| Ascorbic Acid | 100 μM-1 mM | 250 μM |
| Morin | 10 μM-2 mM | 300 μM |
| Glutathione | 50 μM-2 mM | 500 μM |
| Human recombinant insulin | 0.001 to 0.012 mg/ml | 0.006 mg/ml |
| β-hydroxybutyrate | 5 mM-35 mM | 10 mM |

Alternatively or additionally, one or more of several different classes of compounds may also be included in the inventive storage solutions, including growth factors, such as VEGF and EGF, to enhance limited cellular reproduction, and anti-fungal agents. Appropriate anti-fungal agents which are known in the art or to be developed include, without limitation, amphotericin B (commercially available as Fugizone), fluconasole (commercially available as Diflucan), itraconazole (commercially available as Sporanox), and voriconazole (commercially available as Vfend). The appropriate amounts of each of these components to be included in the storage solutions may be determined by routine experimentation. Other such compounds in these classes which are known or to be developed would also be appropriate for inclusion in the storage solutions according to the invention.

As described in detail below, the corneal storage solutions according to the invention provide a medium for storage which results in improved cell viability (health and functioning), structural integrity (size and shape), and cell density (number of cells per square mm) relative to prior art solutions.

Figure 4:
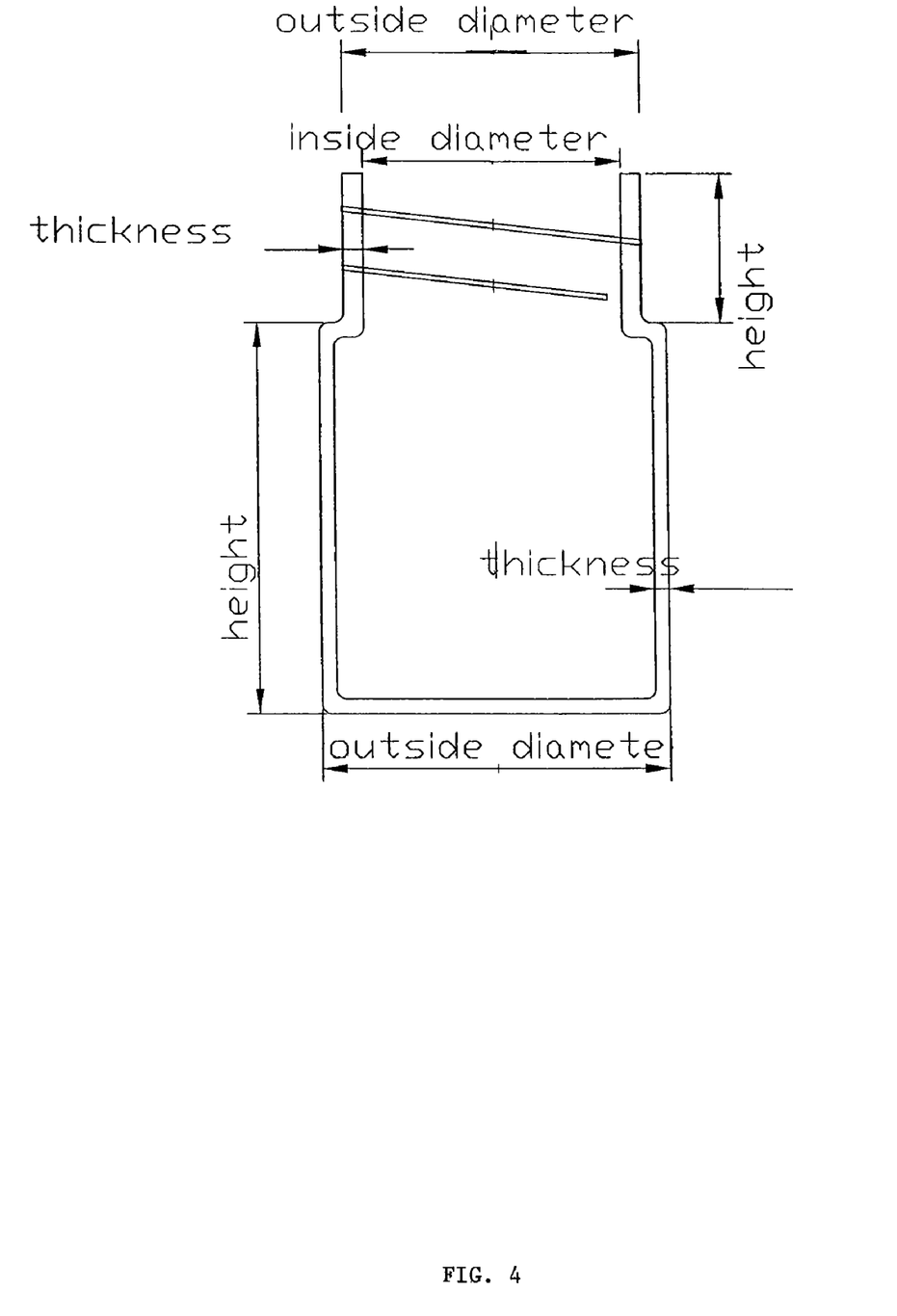
FIG. 4 is a diagram of a vial in a kit according to the invention.

It is preferred that the corneal storage solution according to the invention be packaged in a vial which is configured for receiving, observing, and removing a cornea. As shown in FIG. 4, a preferred vial with such a configuration contains a body and a neck. The neck preferably has an opening (inside diameter) which is large enough to accommodate a corneal scelera measuring about 15 to about 17 mm in diameter, and preferably has an opening diameter of about 22 to about 26 mm, more preferably about 24 mm. A preferred vial is shallow enough to allow a transplant surgeon to easily retrieve the donor material, such as a vial having a total height (including the neck) of about 59 to about 63 mm. For example, a vial having a body height of about 50 mm and a neck height of about 10 mm would be appropriate. The thickness of the glass which comprises the neck is preferably about 2 mm (so that the outside diameter of the neck is about 28 mm), and the thickness of the glass in the body is preferably about 1.2 to about 1.5 mm.

The vial is preferably formed of neutral borosilicate glass, which can be steam sterilized without turning color, leaves no residue after cleaning, and remains optically clear. In order to permit observation and visualization of the corneal endothelium using a specular microscope, the preferred vial has an outside diameter of the body of about 32 to about 36 mm, more preferably about 35 mm. The vial preferably has a bottom which is flat, fire polished, has no distortions, and is optically clear to permit observation of the cornea. The vial preferably contains a solution volume of about 25 to about 30 ml (to the start of the neck).

By packaging the storage solution in a vial with an optically clear bottom, an eye bank technician can view and analyze the cornea directly in the vial, thus minimizing potential contamination.

The preferred vial has several advantages relative to prior art vials. First, it has a larger volume (25 to 30 ml compared with 20 ml). It has been reported that a larger volume of storage solution leads to longer preservation time. The vial also has a larger diameter opening, allowing storage of larger corneal rims (greater than 16 mm). Finally, the larger diameter opening of the vial facilitates easier manipulation of the cornea.

The vial further comprises a top or cap, such as a screw top. The material used to form the top is not critical to the invention provided that it may be sterilized, easy to clean, and free of particulates. For example, the top may be formed of a plastic such as bakelite. The inside of the top is preferably lined with a seal comprising an inert material such as, but not limited to silicone or a fluoropolymer (such as polytetrafluoroethylene). Once the top has been screwed onto the vial, preferably having a thread finish of about 33-400, such a seal makes the vial airtight to preserve its contents.

A kit containing a vial having a flat, optically clear bottom and the corneal storage solution as previously described is also included in the present invention. In one embodiment, the kit further contains instructions for use in preserving corneas prior to in vivo use, such as transplantation or grafting.

The invention also provides a method by which the in vitro storage and preservation of the viability, structural integrity, and cell density of corneal tissues may be effectuated for subsequent use. The method permits a use of the preserved tissue up to at least about two weeks after the date of harvest from the donor, since the viability, structural integrity, and density of the corneal endothelial cells will remain adequate for a period of up to about fourteen days, allowing the tissue to be used for subsequent corneal transplantation or other application.

The method includes at least two steps. First, a cornea is removed from an eye globe of a donor using conventional techniques which are known in the art or to be developed. Then, the cornea is placed in a corneal storage solution as described in detail above. It is preferred that the cornea be maintained in the solution at about 2° C. to about 8° C., more preferably at about 4° C. The corneal tissue to which this method is applied may subsequently be removed from the storage solution and used in other in vitro or in vivo applications for which viable corneal tissue are required, such as cell culture, transplantation and/or grafting therapies.

It has been found that preserving corneal tissue using the methods and solutions of the invention allows for maintenance of the viability, structural integrity, and density of the corneal cells, enhancing the success of any transplantation or grafting procedures which may be subsequently performed using the stored corneal tissue.

The beneficial effects of the corneal storage solutions according to the invention are demonstrated by the following studies. Specifically, studies were performed to compare the efficacy of Optisol™ solution with solutions containing morin, high molecular weight dextran, β-hydroxybutyrate, and insulin by measuring endothelial cell viability and structural integrity using in-vitro and ex-vivo evaluations.

Material and Methods

In-Vitro Studies

Bovine Corneal Endothelial (BCE) cells (ATCC) were cultured in DMEM medium (Dulbecco's Modification of Eagle's Medium) containing 10% FBS, 4 mM L-glutamine, and 1% Penicillin-Streptomycin. Cells were seeded onto 96-well tissue culture plates at $5\times10^4$ cells/well. The plates were incubated for 48 hours at 37° C. in a humidified, 5% $CO_2$ atmosphere. The DMEM medium was removed and 200 µl of the appropriate medium were added to the cells. Cells were then stored at 4° C. for 3, 7, 10, 12, and 14 days. After the appropriate time, the medium was removed and the cells were washed with 100 µl of Hanks Balanced Salt Solution. 1 mM MTT (3-(4,5-dimethylthiazol-2yl)-2,5-diphenyltetrazolium bromide) (Molecular Probes) solution was added to the wells and incubated at 37° C. in a humidified, 5% $CO_2$ atmosphere for 3.5 hours. 70 µl of the MTT solution were removed and 100 µl of DMSO were added. The plates were then read at an absorbance of 540 nm with a plate reader and the percentage of cell viability was determined.

Ex-Vivo Studies

Corneas from freshly slaughtered pigs were used and were stored in either Optisol™ solution (Bausch and Lomb) or a solution according to the present invention (Table 1) for 4, 7, and 14 days at 4° C. Specular microscopy of the corneal endothelium was performed on each cornea before storage and on day 4, day 7, and day 14. The mean endothelial cell area, coefficient of variation (CV), and endothelial cell density were determined from at least 50 endothelial cells per analysis.

Statistics

Data are provided as mean (SD). Statistical analysis was performed by using the Students t-test with $p \leq 0.05$ considered statistically significant.

Results

Figure 1:
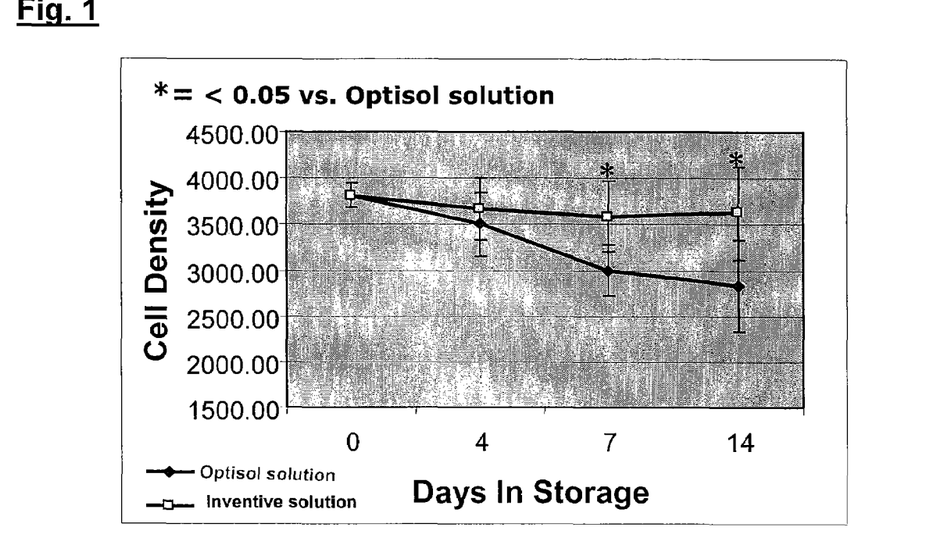
FIG. 1 is a comparative graph of cell density over time for Optisol™ solution and a solution according to the invention.

In one embodiment, the inventive solution contains, in addition to morin and high molecular weight dextran, both β-hydroxybutyrate (preferably about 10 mM) and insulin (preferably about 0.006 mg/ml). To investigate if the combination of morin, high molecular weight dextran, β-hydroxybutyrate, and insulin results in a preservation media which preserves the corneal endothelium better than Optisol™ solution, ex-vivo evaluations were performed. The viability, cell density, structural integrity and cell density of the corneal endothelium were measured for porcine corneas that were stored in either Optisol™ solution or the inventive solution. The mean endothelial cell density for a freshly enucleated porcine cornea is $3811.44 \pm 131.54$ cells/mm². As shown in FIG. 1, the cell density of the endothelial cells stored in Optisol™ solution steadily decreases as storage time increases. However, in the inventive solution, the cell density is maintained at ~3500 cells/mm² for up to 14 days. The cell densities in Optisol™ solution on days 7 and 14 were $2999.65 \pm 272.65$ cells/mm² and $2831.40 \pm 505.21$ cells/mm² respectively, which is statistically lower than the cell density in the inventive solution. Use of the inventive solution thus resulted in an approximately 19.5% improvement in cell density at day 7 and an approximately 32% improvement in cell density at day 14 (FIG. 1).

Corneas stored in the inventive solution also showed an improvement in the viability of corneal endothelium relative to Optisol™ solution. As shown in Table 2, after 14 days of storage in Optisol™, 54.8% of the endothelium is damaged. This is statistically higher than resulted from storage in the inventive solution, which showed approximately 31.7% damage. Compared to Optisol™ solution, the inventive solution thus promotes an approximately 40% improvement in endothelium viability after 14 days of storage.

TABLE 2

% Cell Damage of Porcine Corneal Endothelium

| Item | Day 4 | Day 7 | Day 14 |
|---|---|---|---|
| Optisol ™ solution | 8.88 ± 3.82 | 18.48 ± 6.87 | 54.8 ± 11.6 |
| Inventive Solution | 11.23 ± 6.67 | 20.73 ± 10.58 | 31.7 ± 10.7* |

*indicates <0.05 vs. Optisol solution

Endothelial structural integrity was also evaluated. Polymegethism, a common occurrence during corneal storage, refers to the size variation of corneal endothelial cells. A high occurrence of polymegethism is an indication of structural instability. (See, for example Kohnen *J Cataract Refract Surg;* 24:967-968 (1997); Bourne et al. *IOVS;* 38:779-782 (1997).) Polymegethism is calculated as the standard deviation/average cell area and is expressed as percentage coefficient of variation (% CV), so that a higher CV indicates a less stable cornea.

Figure 2:
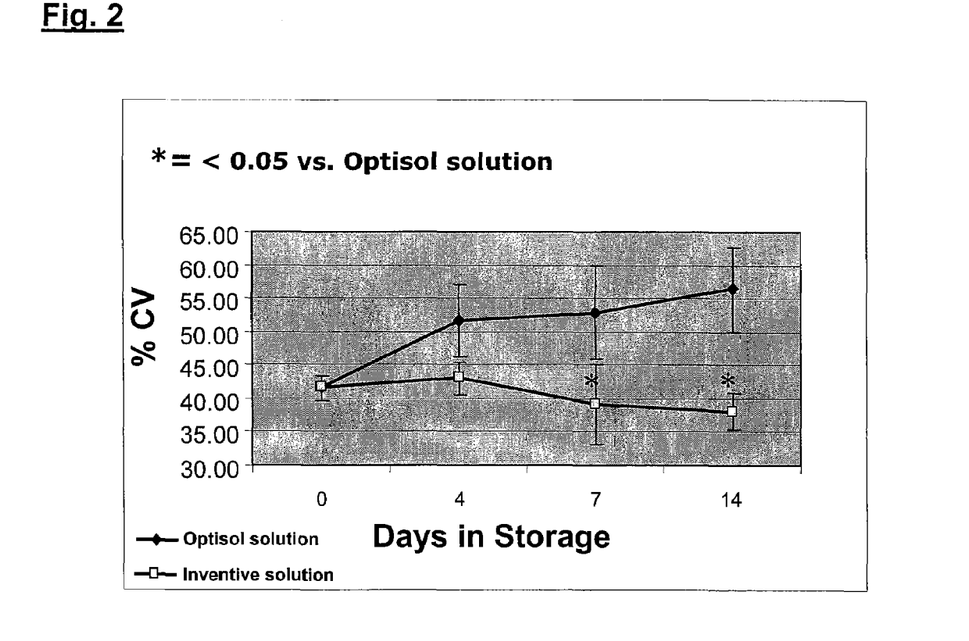
FIG. 2 is a comparative graph of coefficient of variation over time for Optisol™ solution and a solution according to the invention.

The polymegethisms for corneas stored in either Optisol™ solution or the inventive solution were calculated at day 4, day 7, and day 14 of storage time (FIG. 2). The mean % CV for a freshly enucleated porcine cornea was 41.54±1.97%. The % CV for corneas stored in Optisol™ solution increased with storage time, suggesting that the cells were losing structural integrity and that the cornea was less stable. There is no statistical difference in % CV between the inventive solution and Optisol™ solution at day 4. However, there is a 1.2 fold increase in the mean % CV for Optisol™ solution versus the inventive solution (50.65±5.87% vs. 41.19±9.87). At days 7 and 14, the % CV for Optisol™ solution is statistically higher than that of the inventive solution. Specifically, the % CV for Optisol™ solution at day 7 is 52.90±7.02%, a 1.35 fold increase over the inventive solution (39.13±4.59%). At day 14, Optisol™ solution resulted in a 1.48 fold increase over the inventive solution, 56.33±6.51% vs. 38.00±13.93%. These studies thus show that the inventive solution is very effective at sustaining the % CV and at preventing polymegethism, thereby maintaining the structural integrity of the corneal endothelium better than Optisol™ solution.

Figure 3:
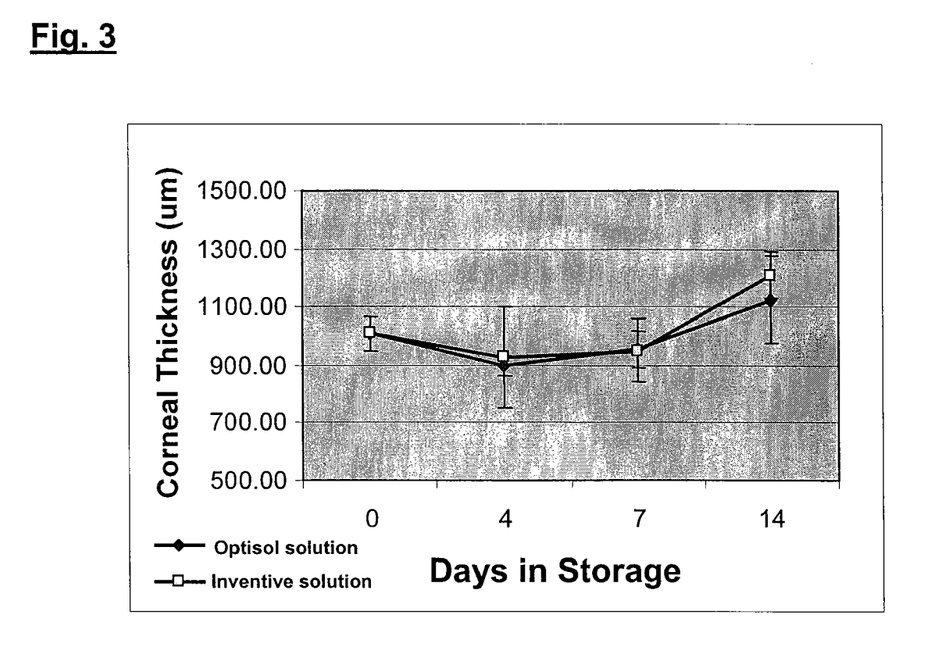
FIG. 3 is a comparative graph of corneal thickness over time for Optisol™ solution and a solution according to the invention.

Prevention of corneal edema is very important during corneal storage. Corneal swelling was determined by measuring the thickness of the corneal endothelium. The mean corneal thickness of a freshly enucleated porcine cornea was 1007.15±61.99 μm. Corneas stored in the inventive solution exhibited corneal thickness measurements similar to those stored in Optisol™ solution (see FIG. 3). There is no statistical difference in corneal thickness measurements at day 4, day 7, or day 14 between corneas stored in Optisol™ solution or the inventive solution, and thus the ability of the inventive solution to prevent corneal edema is similar to that of the known Optisol™ solution.

In conclusion, these studies suggest that a preferred solution according to the invention which contains high molecular weight dextran, morin, β-hydroxybutyrate, and insulin is an effective corneal storage media for corneal preservation. The main advantage of the inventive solutions is their ability to preserve endothelial viability, endothelial cell density and endothelial structural integrity mediated by metabolic pathways induced by, in preferred embodiments, morin, high molecular weight dextran, β-hydroxybutyrate, and insulin. Overall, the storage solutions according to the invention are more effective at preserving corneal tissue, specifically endothelial viability, than Optisol™ solution.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A corneal storage solution comprising:
    a) a buffered, balanced, nutrient and electrolyte aqueous solution,
    b) at least one colloidal osmotic agent comprising high molecular weight dextran having a molecular weight of at least 2,000,000 Daltons,
    c) a phenolic antioxidant,
    d) a non-lactate-generating substrate,
    e) a thiol-containing compound,
    f) insulin, and
    g) at least one antibiotic,
    in amounts effective to maintain cell density and cell viability of corneas stored in vitro for a period of greater than four days up to about two weeks, wherein components (b) to (g) are only required to the extent that they are not included in (a).

2. The corneal storage solution according to claim 1, wherein the high molecular weight dextran has a molecular weight of 2,000,000 Daltons.

3. The corneal storage solution according to claim 1, wherein the at least one colloidal osmotic agent further comprises chondroitin sulfate.

4. The corneal storage solution according to claim 1, wherein the at least one antibiotic is selected from the group consisting of gentamycin, streptomycin, penicillin, erythromycin, and a fluoroquinolone.

5. The corneal storage solution according to claim 1, wherein the phenolic anti-oxidant compound comprises at least one compound selected from the group consisting of resveratrol, fistein, piceatannol, quercetin, butein, rutin, gallic acid, green tea extract, and morin.

6. The corneal storage solution according to claim 5, wherein the phenolic anti-oxidant compound comprises morin.

7. The corneal storage solution according to claim 1, wherein the non-lactate- generating substrate comprises at least one compound selected from the group consisting of β-hydroxybutyrate and derivatives thereof, β-hydroxyhexonate and derivatives thereof, and L-lactide.

8. The corneal storage solution according to claim 7, wherein the non-lactate generating substrate comprises β-hydroxybutyrate.

9. The corneal storage solution according to claim 1, wherein the thiol-containing compound comprises at least one compound selected from the group consisting of N-acetyl-L-cysteine, β-mercaptoethanol, dithiothreitol, and reduced glutathione.

10. The corneal storage solution according to claim 9, wherein the thiol-containing compound comprises reduced glutathione.

11. The corneal storage solution according to claim 1, further comprising at least one component selected from the group consisting of ascorbic acid, calciferol, inositol, inosine, camosine or a derivative thereof, a growth factor, sodium bicarbonate, sodium pyruvate, and L-alanyl-L-glutamine.

12. The corneal storage solution according to claim 1, wherein the solution has a pH of about 7.2 to about 7.4.

13. The corneal storage solution according to claim 1, wherein the nutrient and electrolyte solution comprises M-199.

14. The corneal storage solution according to claim 1, wherein the solution comprises:
(a) M-199;
(b) about 2.5 g/L to about 25 g/L high molecular weight dextran;
(c) about 10 µM to about 2 mM morin;
(d) about 5 mM to about 35 mM β-hydroxybutyrate;
(e) about 50 µM to about 2 mM reduced glutathione;
(f) about 10 g/L to about 75 g/L chondroitin sulfate;
(g) about 0.001 to about 0.012 mg/ml insulin;
(h) about 10 to about 1000 µg/ml gentamycin; and
(i) about 10 to about 1000 µg/ml streptomycin.

15. The corneal storage solution according to claim 14, further comprising at least one component selected from the group consisting of about 0.018 to about 0.176 g/L ascorbic acid, up to about 0.01 g/L inosine, about 3.6 to about 4.4 mM L-alanyl-L-glutamine, about 0.9 to about 1.1 mM sodium pyruvate, up to about 0.0002 g/L calciferol, up to about 0.0001 g/L i-inositol, and about 1.3 to about 2.5 g/L sodium bicarbonate.

16. The corneal storage solution according to claim 14, wherein the solution comprises:
(a) M-199;
(b) about 10 g/L high molecular weight dextran;
(c) about 300 µM morin;
(d) about 10 mM β-hydroxybutyrate;
(e) about 500 µM glutathione;
(f) about 30 g/L chondroitin sulfate;
(g) about 0.006 mg/ml insulin;
(h) about 100 µg/ml gentamycin; and
(i) about 200 µg/ml streptomycin.

17. The corneal storage solution according to claim 16, further comprising at least one component selected from the group consisting of about 0.05 g/L ascorbic acid, about 0.005 g/L inosine, about 4 mM L-alanyl-L-glutamine, about 1 mM sodium pyruvate, about 0.0001 g/L calciferol, about 0.00005 g/L i-inositol, and about 1.7 g/L sodium bicarbonate.

18. A method for in vitro storage and preservation of the viability of human corneal epithelial cells for subsequent use, comprising the steps of:
(a) removing a cornea from an eye globe;
(b) placing the cornea in a corneal storage solution, the solution comprising effective amounts of:
(i) a buffered, balanced, nutrient and electrolyte aqueous solution;
(ii) at least one colloidal osmotic agent comprising high molecular weight dextran having a molecular weight of at least 2,000,000 Daltons;
(iii) a phenolic antioxidant compound;
(iv) a non-lactate-generating substrate;
(v) a thiol-containing compound;
(vi) insulin; and
(vii) at least one antibiotic;
wherein components (ii) to (vii) are only required to the extent that they are not included in (i).

19. The method according to claim 18, wherein the viability of the cells of the cornea is maintained in the solution for a period of greater than about four days up to at least about two weeks.

20. The method according to claim 18, wherein the subsequent use is an in vivo use.

21. The method according to claim 20, wherein the in vivo use is selected from transplantation and grafting.

22. The method according to claim 18, wherein the solution is maintained at about 2° C. to about 8° C.

23. The method according to claim 22, wherein the solution is maintained at about 4° C.

24. A kit comprising:
(a) a vial having a flat, optically clear bottom; and
(b) a corneal storage solution, wherein the corneal storage solution comprises:
(i) a buffered, balanced, nutrient and electrolyte aqueous solution;
(ii) at least one colloidal osmotic agent comprising high molecular weight dextran having a molecular weight of at least 2,000,000 Daltons;
(iii) a phenolic antioxidant compound;
(iv) a non-lactate-generating substrate;
(v) a thiol-containing compound;
(vi) insulin; and
(vii) at least one antibiotic;
in amounts effective to maintain cell density and cell viability of corneas stored in vitro for a period of greater than four days up to about two weeks; wherein components (ii) to (vii) are only required to the extent that they are not included in (i).

25. The kit according to claim 24, wherein the vial comprises neutral borosilicate glass.

26. The kit according to claim 24, wherein the vial further comprises a screw cap having a lining, wherein the screw cap provides an air-tight seal to the vial.

27. The kit according to claim 26, wherein the lining comprises an inert fluoropolymer or silicone.

28. The kit according to claim 24, wherein the vial has a body and a neck, and wherein the body has an outside diameter of about 35 mm and a height of about 50 mm, and wherein the neck has a height of about 10 mm and an inside diameter of about 24 mm.

29. The kit according to claim 24, further comprising instructions for use in preserving corneas prior to in vivo use.

30. A method for reducing corneal swelling in a cornea stored in a corneal storage solution, the method comprising storing a cornea in a solution comprising effective amounts of:
(a) a buffered, balanced, nutrient and electrolyte aqueous solution;
(b) at least one colloidal osmotic agent comprising high molecular weight dextran having a molecular weight of at least 2,000,000 Daltons;
(c) a phenolic antioxidant compound;
(d) a non-lactate-generating substrate;
(e) a thiol-containing compound;
(f) insulin; and
(g) at least one antibiotic;
wherein components (b) to (g) are only required to the extent that they are not included in (a).

* * * * *

UNITED STATES PATENT AND TRADEMARK OFFICE
CERTIFICATE OF CORRECTION

| | | |
|---|---|---|
| PATENT NO. | : 7,601,487 B2 | Page 1 of 1 |
| APPLICATION NO. | : 11/278835 | |
| DATED | : October 13, 2009 | |
| INVENTOR(S) | : Soll et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 479 days.

Signed and Sealed this

Fifth Day of October, 2010

David J. Kappos
*Director of the United States Patent and Trademark Office*